(12) United States Patent
Lin et al.

(10) Patent No.: US 7,242,472 B2
(45) Date of Patent: Jul. 10, 2007

(54) BIOCHIP DETECTION SYSTEM

(75) Inventors: Yan Rung Lin, Hsinchu (CN); Teh Ho Tao, Hsinchu (CN); Zu Sho Chow, Hsinchu (CN); Ding Kun Liu, Hsinchu (CN)

(73) Assignee: Industrial Technology Research Institute, Hsinchu County (TW)

( * ) Notice: Subject to any disclaimer, the term of this patent is extended or adjusted under 35 U.S.C. 154(b) by 455 days.

(21) Appl. No.: 10/866,747

(22) Filed: Jun. 15, 2004

(65) Prior Publication Data

US 2005/0110998 A1     May 26, 2005

(30) Foreign Application Priority Data

Nov. 26, 2003   (TW)   ............................... 92133245 A

(51) Int. Cl.
*G01J 3/30*   (2006.01)
(52) U.S. Cl. ...................................... 356/317; 356/417
(58) Field of Classification Search ................ 356/317, 356/318, 417
See application file for complete search history.

(56) References Cited

U.S. PATENT DOCUMENTS

| | | | |
|---|---|---|---|
| 6,252,717 B1 * | 6/2001 | Grosskopf | 359/619 |
| 6,441,973 B1 * | 8/2002 | Ramm et al. | 359/778 |
| 6,744,502 B2 * | 6/2004 | Hoff et al. | 356/317 |
| 6,970,240 B2 * | 11/2005 | Oldham et al. | 356/317 |
| 6,970,246 B2 * | 11/2005 | Hansen | 356/417 |
| 2003/0160957 A1 * | 8/2003 | Oldham et al. | 356/317 |

* cited by examiner

*Primary Examiner*—Layla G. Lauchman
(74) *Attorney, Agent, or Firm*—Volentine & Whitt, PLLC

(57) ABSTRACT

The present invention discloses a biochip detection system for detecting a biochip labeled with multiple fluorophores. The biochip detection system comprises a broadband light source for generating a light beam, a stand for supporting the biochip, a light integrator positioned between the broadband light source and the biochip, a lens set for adjusting the cross-sectional area of the light beam, a first filter module positioned on the optical path of the light beam, a detector, e.g., CCD camera, photodiode array, for detecting a fluorescence beam emitted from the biochip, and a second filter module positioned on the optical path of the fluorescence beam. The light integrator can be a light tunnel, a lens array or a holographic diffuser for uniforming the intensity distribution of the light beam and changing the cross-sectional shape of the light beam into a rectangle.

14 Claims, 6 Drawing Sheets

BIOCHIP DETECTION SYSTEM

BACKGROUND OF THE INVENTION (A) Field of the Invention

The present invention relates to a biochip detection system, and more particularly, to a biochip detection system using a single broadband light source and capable of fast analysis.

(B) Description of the Related Art

The purpose of sequencing human gene is to identify the function of an individual human gene. Given an understanding of the functions of human genes, researchers may develop therapeutic methods of the treatment for various diseases that affect human beings, particularly therapeutic methods of the treatment for genetic diseases. Hence, the completion of sequencing human gene has a revolutionary impact on the test method used in detecting diseases. For instance, a person's blood is analyzed to check whether the blood contains a biomarker of a specific disease so as to check whether being attacked by a specific disease, wherein the analysis sample can be DNA and proteins, etc.

The detection process of a biochip is the key to the performance of the biochip and thus a very important step with respect to the application of biochips. Confocal laser scanning fluorescence microscopy is widely used in the detection of biochips nowadays since it is characterized in highly precise 3-D resolution for a dramatic improvement of signal-to-noise. However, it possesses a drawback of time-consuming whenever it scans a large area or numerous analysis points through a point-by-point manner. Instead of a point-by-point manner, the intensity of illumination has to be extremely uniform within the analyzing region; otherwise the detection signals can not been relatively quantized. In addition, light sources with different spectrum are required for different fluorescence biomarkers.

FIG. 1 is a schematic diagram of a biochip detection system 10 according to the prior art, wherein the biochip detection system 10 analyzes biochips by the confocal laser scanning fluorescence microscopy. As shown in FIG. 1, the biochip detection system 10 uses a red beam 32a and a green beam 32b generated by a red laser 12a and a green laser 12b, respectively. The red beam 32a transites a first dichroic mirror 16, while the green beam 32b is reflected by the first dichroic mirror 16. Both the red beam 32a and the green beam 32b are then reflected by a second dichroic mirror 18, and focused on a biochip 22 by means of an objective lens 20. The red beam 32a and the green beam 32b illuminating on the biochip 22 excite the biomarkers on the biochip 22 to emit a first fluorescence 34a and a second fluorescence 34b, respectively. The first fluorescence 34a and the second fluorescence 34b pass through the objective lens 20, a pinhole 23 and the second dichroic mirror 18 in sequence and then reach a third dichroic mirror 24. The first fluorescence 34a transites the third dichroic mirror 24 and a red filter 28a, and is then detected by a first photo-multiplier tube 30a for measuring the intensity. The second fluorescence 34b is reflected by the third dichroic mirror 24 and transites a green filter 28b in advance, and is detected by a second photo-multiplier tube 30b for measuring the intensity.

In the conventional biochip detection system 10, laser beams of two different wavelengths are illuminated on the biochip 22 to excite the biomarker to emit fluorescence, noise is filtered out at the focus by means of the pinhole 23, and the fluorescence intensity of the two fluorescence 34a, 34b are then detected by two photo-multiplier tubes 30a, 30b. The overall cost of the conventional biochip detection system 10 is rather high. Furthermore, the above-mentioned confocal laser scanning fluorescence microscopy analyzes the sample in a point-by-point manner, thus it will be very time-consuming whenever it scans a large area or a microarray biochip with numerous detection points.

SUMMARY OF THE INVENTION

The objective of the present invention is to provide a biochip detection system with a single broadband light source and capable of fast analysis.

In order to achieve the above-mentioned objectives, and avoid the problems of the prior art, the present invention provides a biochip detection system for detecting a sample labeled with multiple fluorophores. The biochip detection system comprises a broadband light source for generating a light beam, a stand for supporting a sample labeled with multiple fluorophores, a light integrator positioned between the broadband light source and the sample, a lens set for adjusting the cross-sectional area of the light beam, a first filter module positioned on the optical path of the light beam, a detector for detecting a fluorescence beam emitted from the sample, and a second filter module positioned on the optical path of the fluorescence beam. The light integrator can be a light tunnel, a lens array or a holographic diffuser for uniforming the intensity distribution of the light beam and changing the cross-sectional shape of the light beam into a rectangle. The first filter module is used for filtering a light with a certain wavelength from the light beam, while the second filter module is used for filtering the fluorescence beam with a certain wavelength from a scattering light from the sample. The scattering light includes the light beam reflected by the sample and the fluorescence beam emitted from the sample excited by fluorophores. The detector can be a CCD camera or photodiode array.

The first filter module can be positioned between the broadband light source and the sample, and the second filter module can be positioned between the sample and the detector. The first filter module includes a first light filter for filtering a first wavelength light from the light beam, a second light filter for filtering a second wavelength light from the light beam, and a first moving device for moving the first light filter or the second light filter onto the optical path of the light beam. The second filter module includes a first fluorescence filter for filtering a first wavelength fluorescence from the scattering light from the sample, a second fluorescence filter for filtering a second wavelength fluorescence from the scattering light from the sample, and a second moving device for moving the first fluorescence filter or the second fluorescence filter onto the optical path of the scattering light.

Compared with the prior art, the biochip detection system of the present invention needs only one broadband light source and only one detector. In addition, the biochip detection system acquires the entire fluorescence image of the sample by only one single direction scanning so that the detection rate is increased.

BRIEF DESCRIPTION OF THE DRAWINGS

Other objectives and advantages of the present invention will become apparent upon reading the following descriptions and upon reference to the accompanying drawings in which.

DETAILED DESCRIPTION OF THE INVENTION

Figure 1:
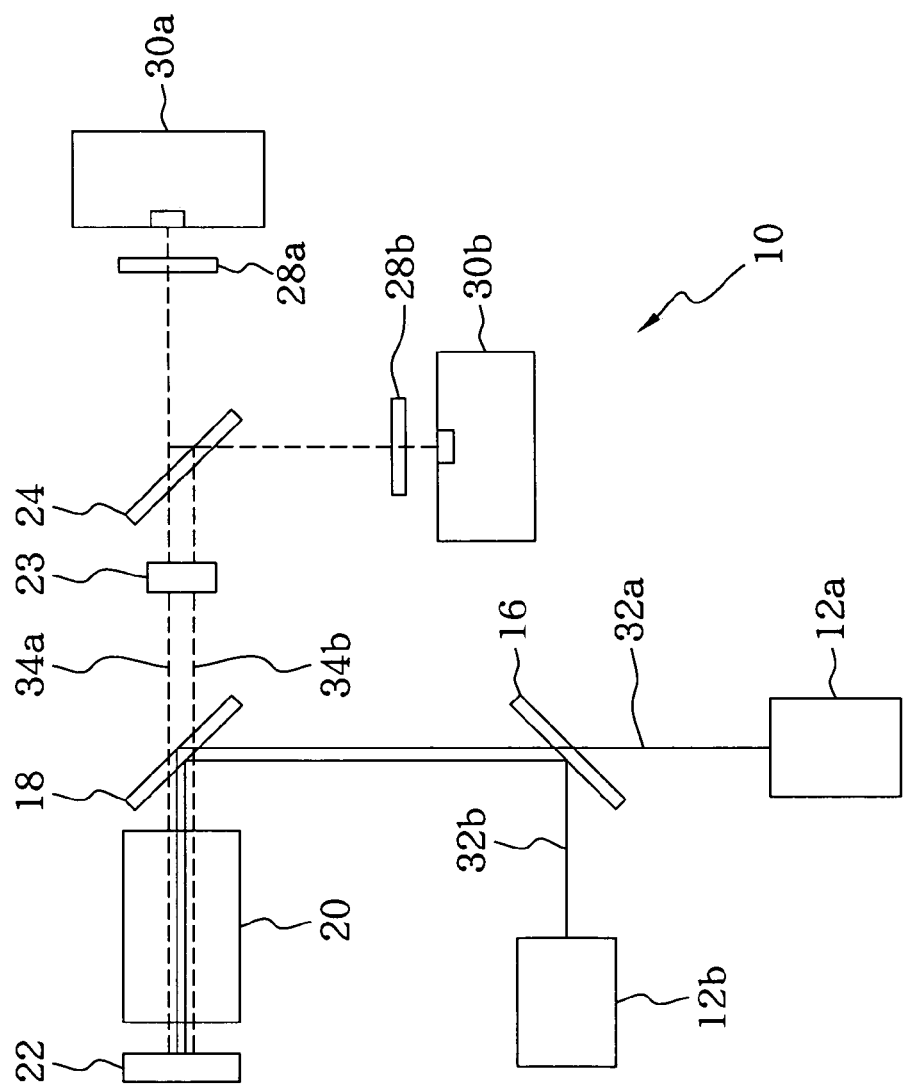
FIG. 1 is a schematic diagram of a biochip detection system according to the prior art.
Figure 2:
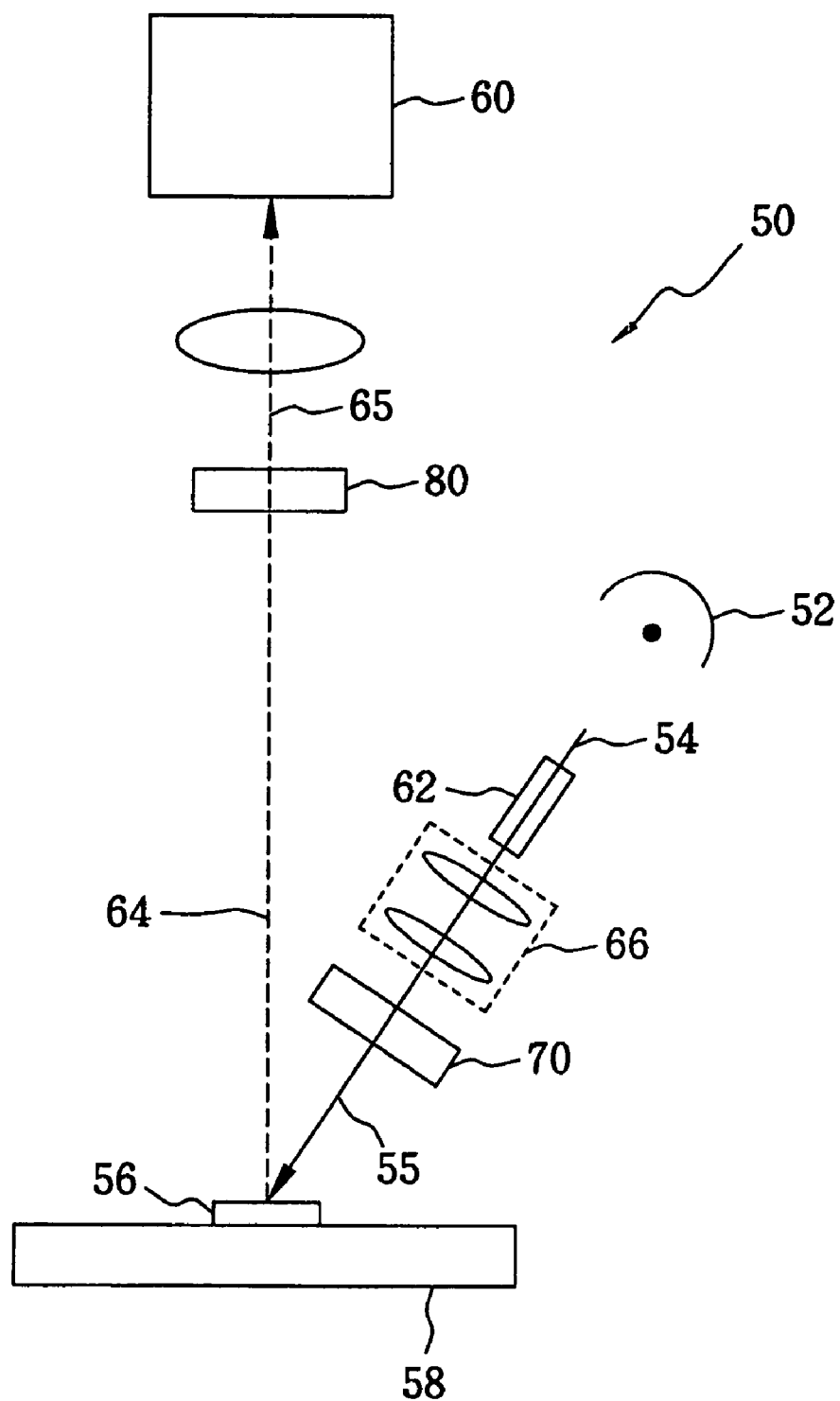
FIG. 2 is a schematic diagram of a biochip detection system according to the first embodiment of the present invention.

FIG. 2 is a schematic diagram of a biochip detection system 50 according to the first embodiment of the present invention. As shown in FIG. 2, the biochip detection system 50 comprises a broadband light source 52 for generating a light beam 54, a stand 58 for supporting a sample 56 (a biochip) labeled with multiple fluorophores, a light integrator 62 positioned between the broadband light source 52 and the sample 56, a lens set 66 for adjusting the cross-sectional area of the light beam 54, a first filter module 70 positioned on the optical path of the light beam 54 for filtering a light beam 55 with a desired wavelength, a detector 60 for detecting a fluorescence beam 65 emitted from the sample 56, and a second filter module 80 positioned on the optical path of the scattering light 64 for filtering the fluorescence beam 65 from the sample 56. The scattering light 64 from the sample 56 includes the light beam 55 scattered by the sample 56 and the fluorescence beam 65 emitted from fluorophores on the sample 56, and the second filter module 80 is positioned on the optical path of the fluorescence beam 65. The light integrator 62 can be a light tunnel, a lens array or a holographic diffuser for uniforming the intensity distribution of the light beam 54 and changing the cross-sectional shape of the light beam 54 into a rectangular. The detector 60 can be a CCD camera or photodiode array.

An acute angle is formed between the surface of the sample 56 and the optical path of the light beam 55 to prevent the reflection beam of the light beam 55 from irradiating on the second filtering module 80 and the detector 60. Consequently, the fluorescence beam 65 detected by the charge-coupling detector 60 has a better signal-to-noise ratio. The broadband light source 52, such as the Ultra High Pressure Lamp (UHP lamp), is characterized in its stability, high luminous flux and high lumen efficiency. The spectrum of the mercury atom transition lines of the UHP lamp is found at 350-450 nm and 540-590 nm. The first filter module 70 is used for filtering the light beam 55 with a certain wavelength from the light beam 54, while the second filter module 80 is used for filtering the fluorescence beam 65 with a certain wavelength from the scattering light 64 from the sample 56. The light beam 55 filtered by the first filter module 70 is capable of exciting fluorophores on the sample 56 to emit the fluorescence beam 65, and the second filter module 80 only allows the fluorescence beam 65 exactly emitted by the fluorophore to pass through.

Figure 3:
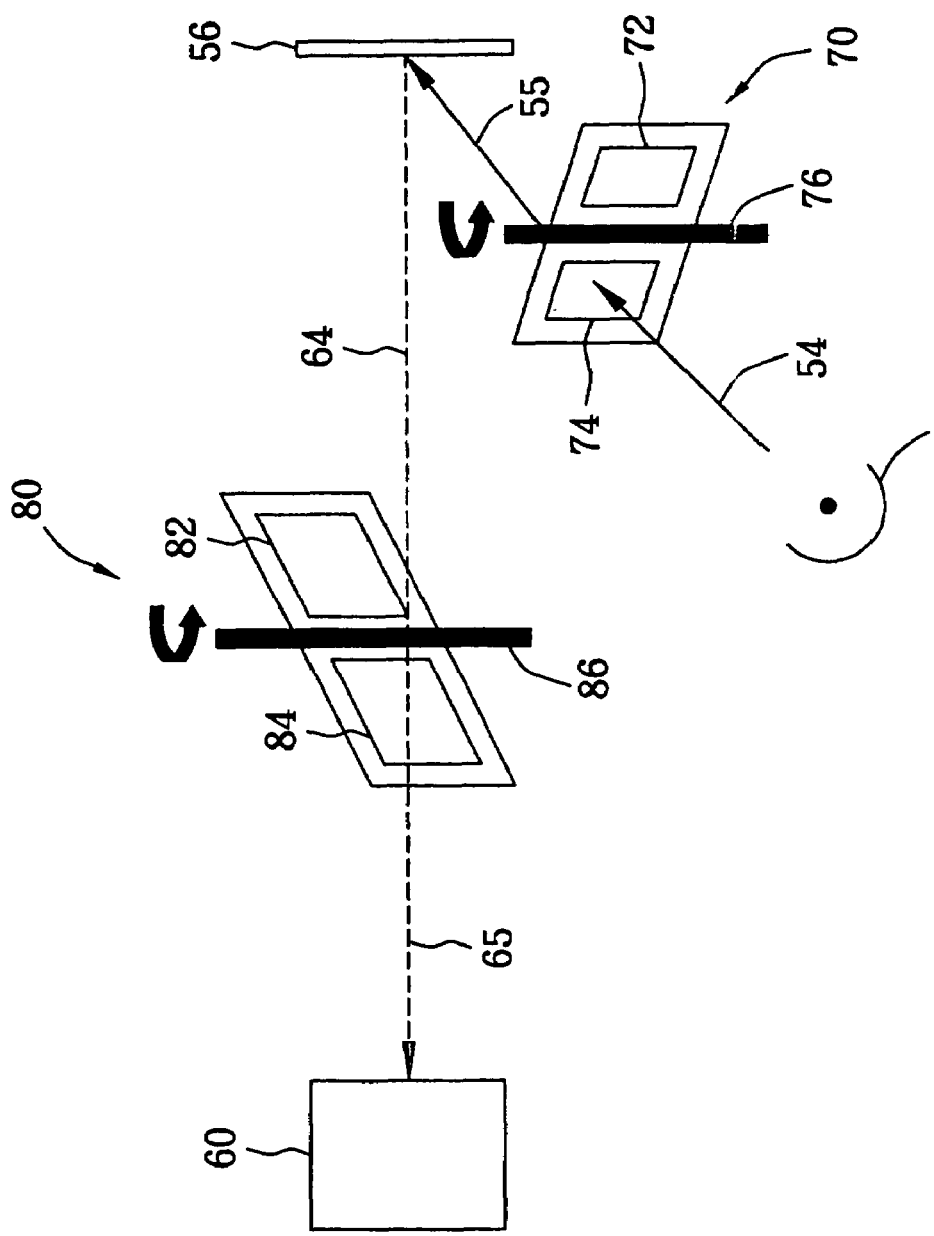
FIGS. 3 and 4 show a portion of a biochip detection system according to the first embodiment of the present invention.
Figure 4:
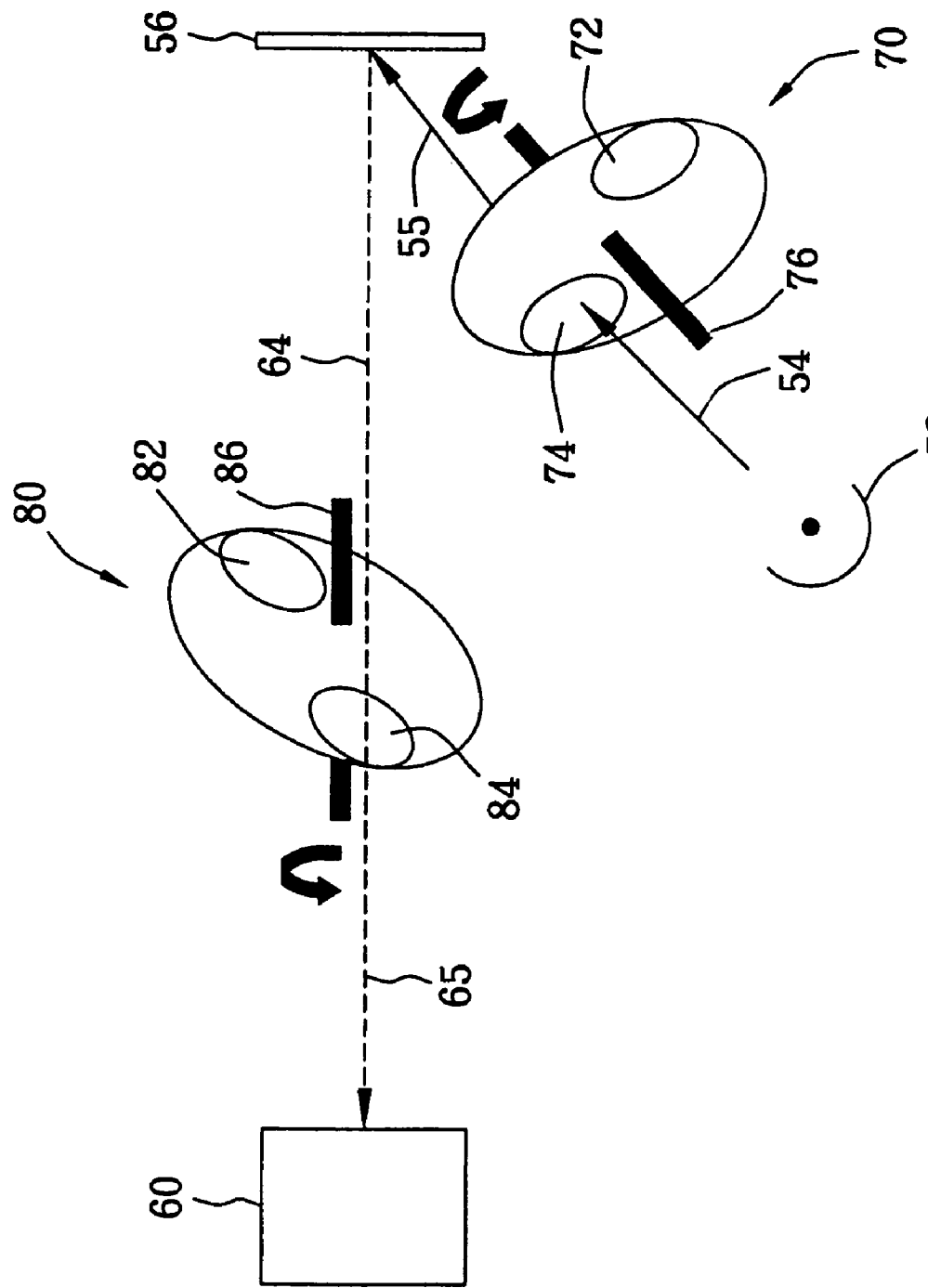

FIG. 3 and FIG. 4 show a portion of the biochip detection system 50 according to the present invention. As shown in FIG. 3, the first filter module 70 is preferably positioned between the broadband light source 52 and the sample 56, while the second filter module 80 is preferably positioned between the sample 56 and the charge-coupling detector 60. The first filter module 70 includes a first light filter 72 for filtering a first wavelength light from the light beam 54, a second light filter 74 for filtering a second wavelength light from the light beam 54, and a first moving device 76 for moving the first light filter 72 or the second light filter 74 onto the optical path of the light beam 54. The second filter module 80 includes a first fluorescence filter 82 for filtering a first wavelength fluorescence from the scattering light 64 from the sample 56, a second fluorescence filter 84 for filtering a second wavelength fluorescence from the scattering light 68 from the sample 56, and a second moving device 86 for moving the first fluorescence filter 82 or the second fluorescence filter 84 onto the optical path of the scattering light 64. Both the first moving device 76 and the second moving device 86 can be a rotational shaft perpendicular to the optical path of the light beam 54 or the scattering light 64, respectively, and a suitable filter can be moved onto the optical path by the rotation of the rotational shaft. In addition, both the first moving device 76 and the second moving device 86 can be a rotational shaft parallel to the optical path, as shown in FIG. 4.

Figure 5:
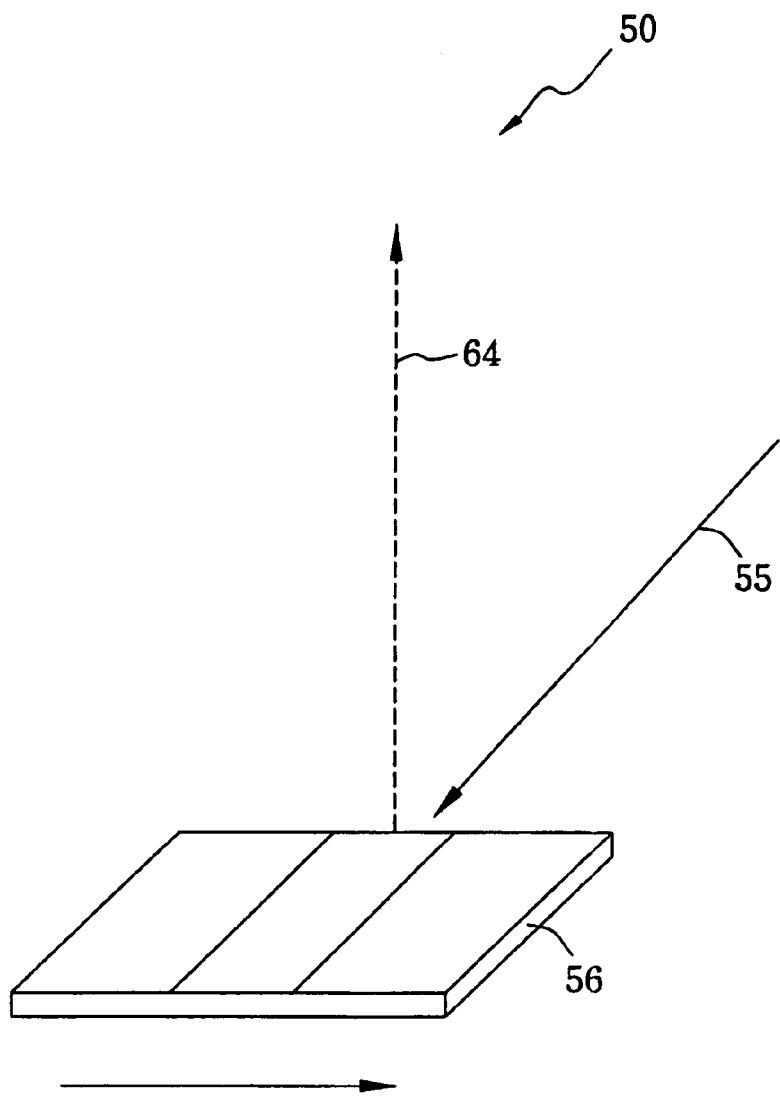
FIG. 5 is a schematic diagram showing the scanning of a sample according to the present invention.

FIG. 5 is a schematic diagram showing the biochip detection system 50 scanning the sample 56 according to the present invention. As shown in FIG. 5, the light beam 55 is filtered from the light beam 54 by the first filter module 70 and then illuminates on a stripe-shaped region of the sample 56, wherein the width of the stripe-shaped region is the same as that of the sample 56. The light beam 55 excites the fluorophore on the sample 56 to emit the scattering light 64 including the fluorescence beam 65, which is then detected by the charge-coupling detector 60. As a result, the biochip detection system 50 needs to perform a single scanning in the direction indicated by the arrow to acquire the entire fluorescence image generated by the sample 56 under the excitation of the light beam 55.

Figure 6:
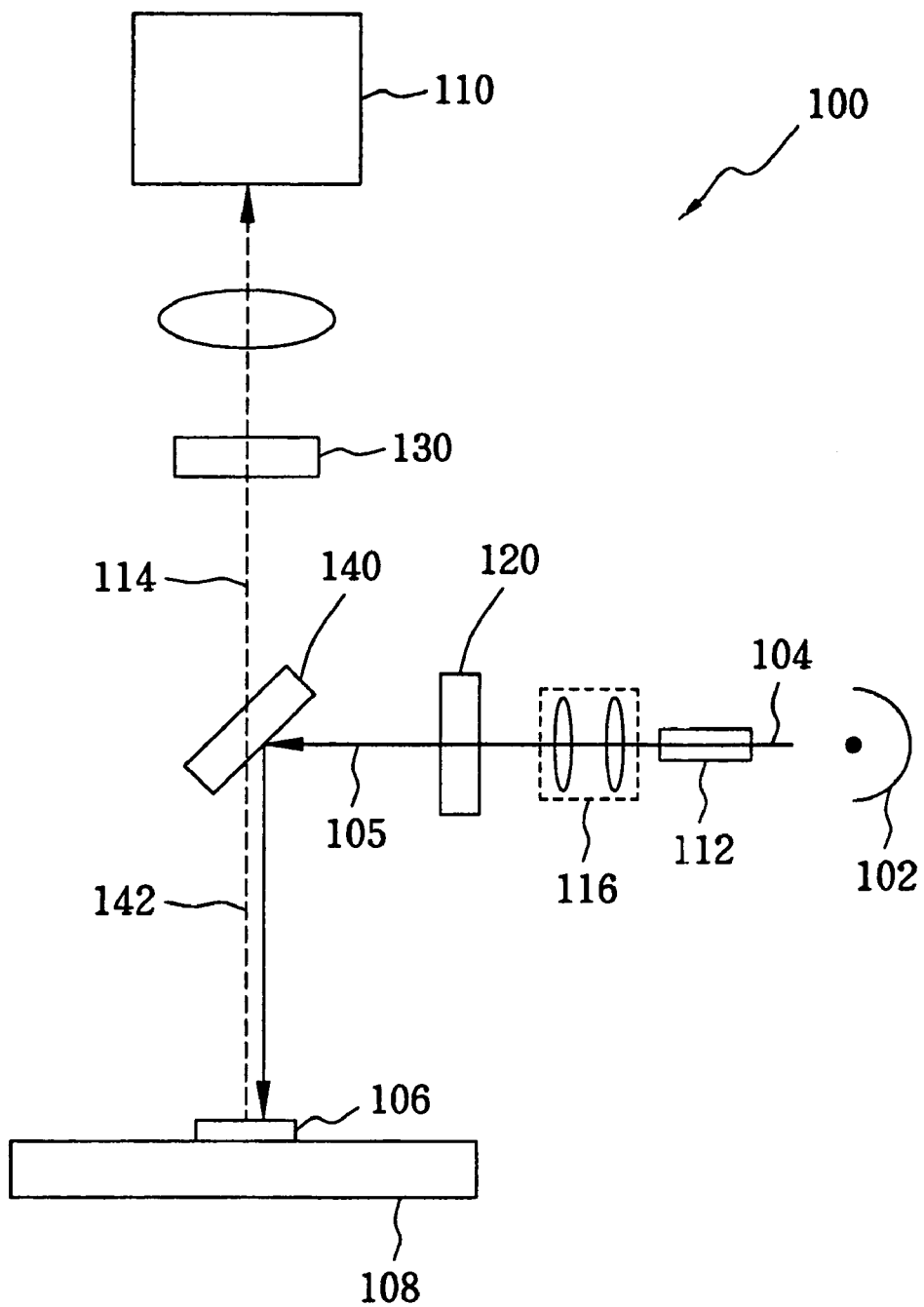
FIG. 6 is a schematic diagram of a biochip detection system according to the second embodiment of the present invention.

FIG. 6 is a schematic diagram of a biochip detection system 100 according to the second embodiment of the present invention. As shown in FIG. 6, the biochip detection system 100 comprises a broadband light source 102 for generating a light beam 104, a stand 108 for supporting a sample 106, a light integrator 112 positioned between the broadband light source 102 and the sample 106, a lens set 116 for adjusting the cross-sectional area of the light beam 104, a dichroic mirror 140 for guiding the light beam 104 to the sample 106, a first filter module 120 positioned on the optical path of the light beam 104 for filtering a light beam 105 with a desired wavelength, a detector 110 for detecting a fluorescence beam 114 emitted by fluorophores on the sample 106, and a second filter module 130 positioned on the optical path of the scattering light 142 for filtering the fluorescence beam 114. The light integrator 112 can be a light tunnel, a lens array or a holographic diffuser for uniforming the intensity distribution of the light beam 104 and changing the cross-sectional shape of the light beam 104 into a rectangular. The scattering light 142 from the sample 106 includes the light beam 105 reflected by the sample 106 and the fluorescence beam 114 emitted by fluorophores on the sample 106. When attempting to detect fluorescence beams of different wavelengths from the sample 106, the dichroic mirror 140 and the second filter module 130 rotates to allow the desired fluorescence beam to pass through and reflect the others, i.e., the dichroic mirror 140 and the second filter module 130 together filter the fluorescence beam 114 from the scattering light 142.

The biochip detection system 100 uses the dichroic mirror 140 to turn the direction of the light beam 105 onto the sample 106 in a very small angle, i.e., the surface of the sample 106 is almost perpendicular to the optical path of the light beam 105. The fluorescence beam 114 emitted from the sample 106 illuminates on the dichroic mirror 140, and preferably, the dichroic mirror 140 allows the passage of the fluorescence beam 114 only and reflects the light beam 105.

Compared with the prior art, the biochip detection system 50 of the present invention possesses the following advantages:

1. Since the first filter module 70 can filter a light with a certain wavelength from the light beam 54, the biochip detection system 50 of the present invention merely needs a broadband light source 52.
2. Since the second filter module 80 can filter the fluorescence beam 65 with the desired wavelength from the scattering light 64 from the sample 56, the biochip detection system 50 of the present invention merely needs a detector 60.
3. The light beam 55 illuminates on a stripe-shaped area of the sample 56, and the width of the stripe-shaped area is the same as that of the sample 56. As a result, the present invention needs to perform a single scanning in one direction to acquire the entire fluorescence image generated by the sample 56 under the excitation of the light beam 55. Consequently, the biochip detection system 50 of the present invention works faster, compared with the prior art analyzing a sample in a point-by-point manner.

The above-described embodiments of the present invention are intended to be illustrative only. Numerous alternative embodiments may be devised by those skilled in the art without departing from the scope of the following claims.

What is claimed is:

1. A biochip detection system, comprising:
    a broadband light source for generating a light beam;
    a stand for supporting a biochip such that an acute angle is formed between the surface of the biochip and the optical path of the light beam;
    a light integrator positioned between the broadband light source and the biochip for uniforming the intensity distribution of the light beam and shaping the cross-section of the light beam into a rectangular shape, wherein the light integrator is a light tunnel or a lens array;
    a lens set for adjusting the cross-sectional area of the light beam;
    a first filter module positioned on the optical path of the light beam;
    a detector for detecting a fluorescence beam emitted from the biochip; and
    a second filter module positioned on the optical path of the fluorescence beam.

2. The biochip detection system of claim 1, wherein the first filter module is positioned between the broadband light source and the biochip.

3. The biochip detection system of claim 1, wherein the first filter module comprises:
    a first light filter for filtering a first wavelength light from the light beam;
    a second light filter for filtering a second wavelength light from the light beam; and
    a first moving device for moving the first light filter or the second light filter onto the optical path of the light beam.

4. The biochip detection system of claim 1, wherein the first filter module comprises at least two filters for filtering at least two lights with different wavelengths from the light beam to excite fluorophores on the biochip.

5. The biochip detection system of claim 1, wherein the second filter module is positioned between the biochip and the detector.

6. The biochip detection system of claim 1, wherein the second filter module comprises:
    a first fluorescence filter for filtering a first wavelength fluorescence from a scattering light from the biochip;
    a second fluorescence filter for filtering a second wavelength fluorescence from the scattering light; and
    a second moving device for moving the first fluorescence filter or the second fluorescence filter onto the optical path of the scattering light.

7. The biochip detection system of claim 1, wherein the second filter module comprises at least two filters for filtering at least two fluorescences with different wavelengths from a scattering light from the biochip.

8. A biochip detection system, comprising:
    a broadband light source for generating a light beam;
    a stand for supporting a biochip such that the surface of the biochip is almost perpendicular to the optical path of the light beam;
    a light integrator positioned between the broadband light source and the biochip for uniforming the intensity distribution of the light beam and shaping the cross-section of the light beam into a rectangular shape, wherein the light integrator is a light tunnel or a lens array;
    a lens set for adjusting the cross-sectional area of the light beam;
    a dichroic mirror for guiding the light beam to the biochip;
    a first filter module positioned on the optical path of the light beam;
    a detector for detecting a fluorescence beam emitted from the biochip; and
    a second filter module positioned on the optical path of the fluorescence beam.

9. The biochip detection system of claim 8, wherein the first filter module is positioned between the broadband light source and the dichroic mirror.

10. The biochip detection system of claim 8, wherein the first filter module comprises at least two filters for filtering at least two lights with different wavelengths from the light beam to excite fluorophores on the biochip.

11. The biochip detection system of claim 8, wherein the first filter module comprises:
    a first light filter for filtering a first wavelength light from the light beam;
    a second light filter for filtering a second wavelength light from the light beam; and
    a first moving device for moving the first light filter or the second light filter onto the optical path of the light beam.

12. The biochip detection system of claim 8, wherein the second filter module is positioned between the detector and the dichroic mirror.

13. The biochip detection system of claim 8, wherein the second filter module comprises at least two filters for filtering at least two fluorescences with different wavelengths from a scattering light from the biochip.

14. The biochip detection system of claim 8, wherein the second filter module comprises:
    a first fluorescence filter for filtering a first wavelength fluorescence from a scattering light from the biochip;
    a second fluorescence filter for filtering a second wavelength fluorescence from the scattering light from the biochip; and
    a second moving device for moving the first fluorescence filter or the second fluorescence filter onto the optical path of the scattering light.

* * * * *

UNITED STATES PATENT AND TRADEMARK OFFICE
CERTIFICATE OF CORRECTION

PATENT NO. : 7,242,472 B2  Page 1 of 1
APPLICATION NO. : 10/866747
DATED : July 10, 2007
INVENTOR(S) : Lin et al.

It is certified that error appears in the above-identified patent and that said Letters Patent is hereby corrected as shown below:

Title page, item (75), change "(CN)" to --(TW)-- (all occurrences).

Signed and Sealed this

Sixteenth Day of October, 2007

JON W. DUDAS
*Director of the United States Patent and Trademark Office*